United States Patent [19]
Rubinstein

[11] Patent Number: 6,080,115
[45] Date of Patent: Jun. 27, 2000

[54] BONE MARROW BIOPSY NEEDLE

[76] Inventor: Alan I. Rubinstein, 100 S. Doheny Dr., Apt. 301, Los Angeles, Calif. 90048

[21] Appl. No.: 09/256,531

[22] Filed: Feb. 24, 1999

[51] Int. Cl.[7] ........................................................ A61B 5/00
[52] U.S. Cl. .............................................................. 600/567
[58] Field of Search ........................... 600/562, 564–567; 606/167, 170, 180

[56] References Cited

U.S. PATENT DOCUMENTS

| | | | |
|---|---|---|---|
| 1,867,624 | 7/1932 | Hoffman | 600/567 |
| 3,007,471 | 11/1961 | McClune | 600/567 |
| 5,357,974 | 10/1994 | Baldridge | 600/567 |
| 5,595,186 | 1/1997 | Rubinstein et al. | 600/567 |

*Primary Examiner*—Max Hindenburg
*Attorney, Agent, or Firm*—Ostrolenk, Faber, Gerb & Soffen, LLP

[57] ABSTRACT

A biopsy needle, suitable for obtaining bone marrow biopsy cores, includes an outer tube member having a lumen extending therethrough, and at a distal end of the outer tube member an opening is provided for receiving a biopsy core. At the distal end, the outer tube member is generally oval in cross-section and thereby has an elongated dimension and a narrow dimension. An inner tube member is slidable and rotatable in the lumen of the outer tube member and has a set of pincers at its distal end. With the inner tube member slid through the lumen of the outer tube member and the pincers positioned at the distal end of the outer tube member and aligned with the elongated dimension, the pincers are in an open position. However, the pincers can be closed thereby to grasp and cut a biopsy core by rotating the inner tube member so that the pincers are aligned with the narrow dimension of the outer tube member. In another embodiment of the biopsy needle, the distal end of the outer tube member has two spaced apart projections extending in the lumen, and by cooperation with these projections, the pincers of the inner tube member can be opened or closed to grasp a biopsy core.

28 Claims, 2 Drawing Sheets

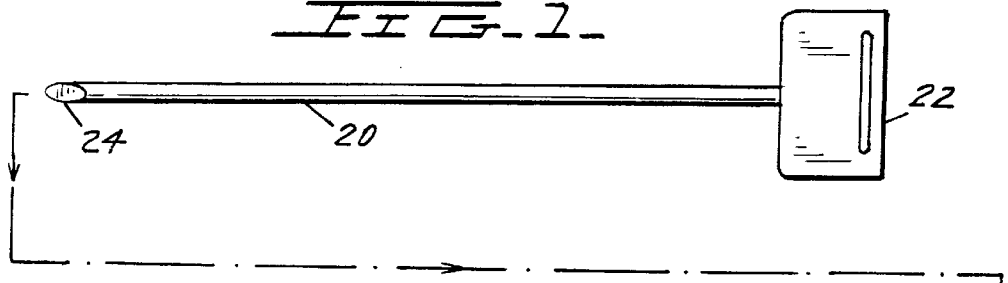
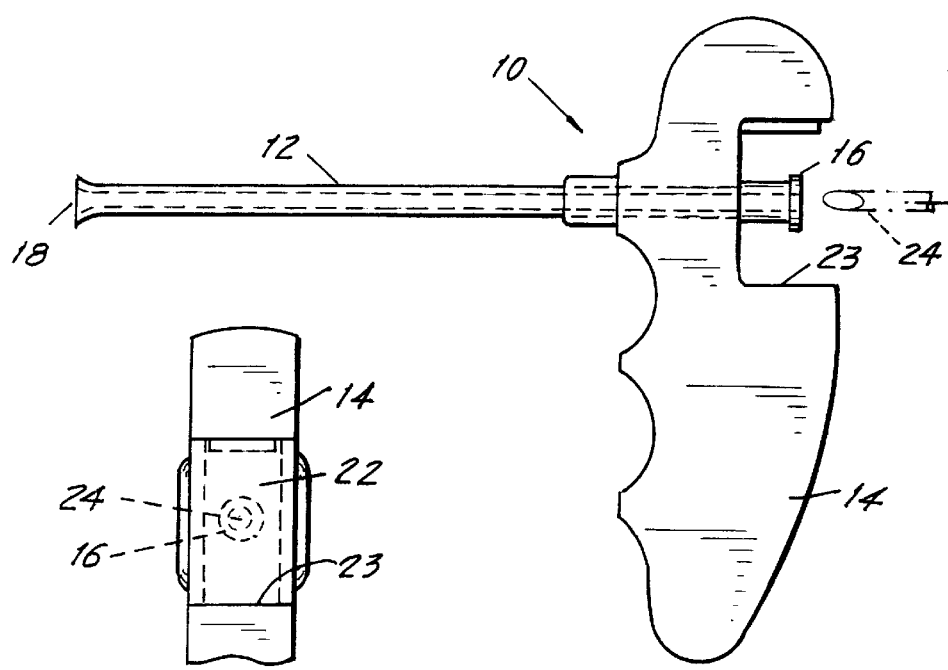
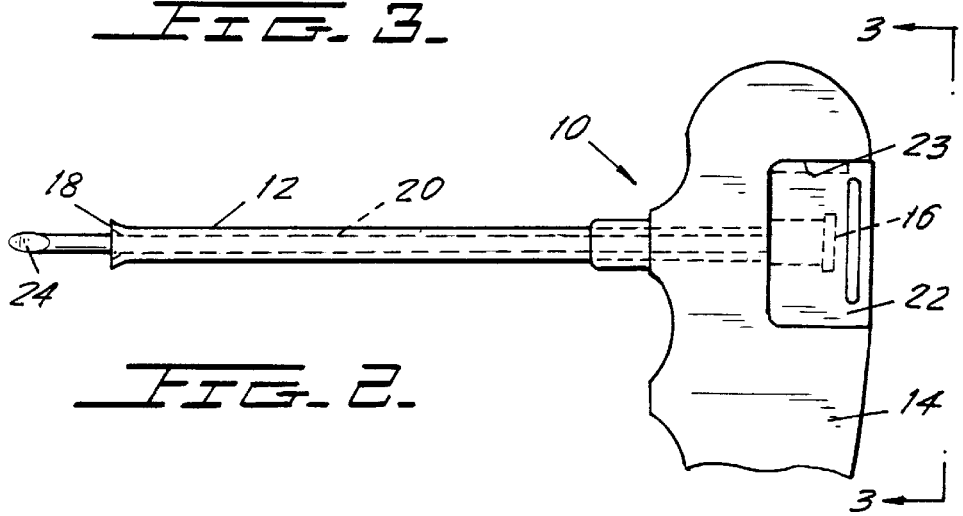

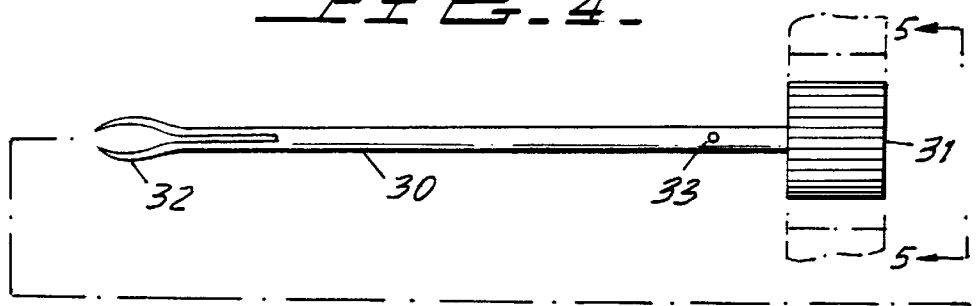
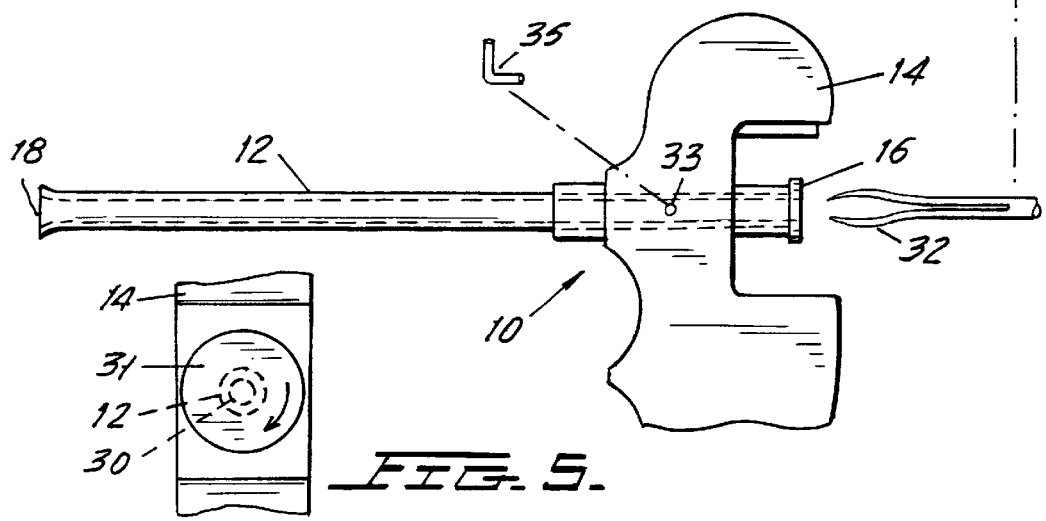
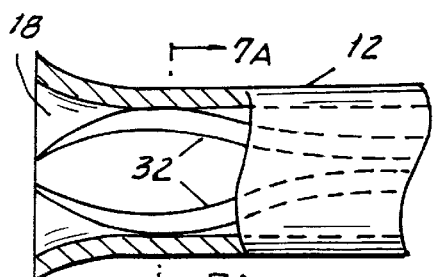
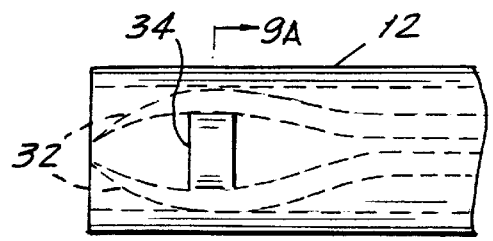
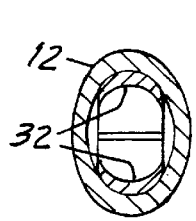
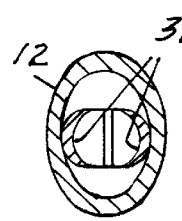
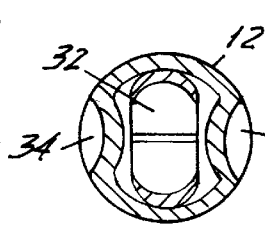
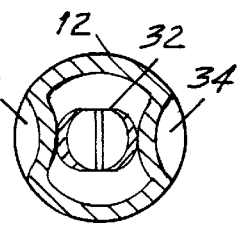

BONE MARROW BIOPSY NEEDLE

FIELD OF THE INVENTION

The present invention relates in general to biopsy needles of the type used to obtain bone marrow biopsies, and more particular to biopsy needles having a more efficient mechanism for grasping and withdrawing a biopsy core from a patient.

BACKGROUND OF THE INVENTION

U.S. Pat. No. 5,462,062 shows in FIGS. 5A–5E a bone marrow biopsy needle including an outer tube with an inwardly tapered distal end and an inner tube with a pair of opposed blades hinged to the inner tube at its distal end. The inner tube is slidable axially within the outer tube. At the distal end of the outer tube, the taper defines a dead space radially outward of the needle opening, and the blades have an open position in which they are contained within the dead space.

The outer tube is inserted into the bone being biopsied with the blades retracted into the dead space so as not to obstruct the entry of the biopsy core into the space within the outer and inner tubes. The outer tube is sharp to make entry into the bone as easy as possible. When the area which is to be biopsied has been entered, the inner tube is pressed axially in the distal direction. The blades engage the tapered end of the outer tube which folds them radially inward on their hinges, which simultaneously cuts off the biopsy core and retains it within the needle. A detent and blocking arrangement is provided for holding the inner and outer tubes in various positions relative to one another.

Although the above-described biopsy needle is effective and greatly improves the ease and security of the bone marrow biopsy process, it is desirable to make further improvements by reducing the number of moving parts, the manufacture of the biopsy needle, and the efficiency of its operation. More particularly, it is desirable to simplify the hinge arrangement, as well as the detent and blocking arrangement.

SUMMARY OF THE INVENTION

An object of the present invention is to provide a biopsy needle suitable for obtaining bone marrow biopsies, which is easier to operate and less complicated in structure than the above-described biopsy needle.

A further objective of the present invention is to provide a biopsy needle which is more economical and simpler to manufacture than the above-described biopsy needle.

According to a first embodiment of the invention, the biopsy needle includes an outer tube member having a lumen extending therethrough with a proximal end and a distal end, and with an opening at the distal end. In the region of the distal end of the outer tube member, the tube is generally oval in cross-section and thus has an elongated dimension and a narrow dimension. Slidable and rotatable within the lumen of the outer tube member is an inner tube member. The inner tube member has pincers at its distal end which can be slid toward the distal end of the outer tube member. If the pincers are positioned proximate the distal end of the outer tube member and in the elongated position, the pincers are in an open position relative to each other. When the inner tube member is rotated, however, so that the pincers are aligned with the narrow dimension, the pincers are in a closed position and thereby are capable of grasping a biopsy core.

A further embodiment of the biopsy needle also includes an outer tube member and an inner tube member. But instead of the distal end of the outer tube member being oval in cross-section, it includes oppositely disposed projections which extend into the lumen. Thus, when the pincers of the inner tube member are positioned at or approximate the distal end of the outer tube member but not in contact with the projections, the pincers are permitted to spread apart and are therefore in their open position. But if the operator rotates the inner tube member so that the pincers contact the projections, the pincers are caused to close upon each other and thereby grasp a biopsy core.

BRIEF DESCRIPTION OF THE DRAWINGS

FIG. 1 is an exploded side view of an outer tube member and a stylet which form part of the biopsy needle;

FIG. 2 is a side view showing the stylet inserted into the outer tube member;

FIG. 3 is a partial end view taken along the line 3—3 of FIG. 2;

FIG. 4 is a side view of an inner tube member, which forms a further part of the biopsy needle, in relationship to the outer tube member;

FIG. 5 is a partial end view taken along the line 5—5 of FIG. 4;

FIGS. 6 and 8 are side views of pincers of the inner tube member in relationship to the outer tube member;

FIGS. 7A, 7B, 9A and 9B, are cross-sectional views taken along the respective lines 7A—7A and 9A–9B of FIGS. 6 and 8 respectively.

DETAILED DESCRIPTION OF THE INVENTION

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

FIGS. 1–6 show a bone marrow biopsy needle 10 having an outer tube member 12 affixed to a handle 14. The outer tube member 12 is hollow throughout its entire length and has a proximal end 16 and a distal end 18. Proximal end 16 is disposed in an opening 23 in handle 14. As shown in FIG. 1, a stylet 20 has a connecting member 22 at its proximal end and a bevelled chisel end 24 at its distal end. As is shown in FIG. 2, the stylet 20 is slid through the lumen of outer tube member 10 so that the bevelled chiseled end 24 extends past the distal end 18 of outer tube member 12. The connecting member 22 cooperates with the handle 14 to securely position the stylet 20 thereto.

The distal end 18 of outer tube member 12 has a tapered angle which is advantageously similar to or the same as that of the bevelled chiseled end 24 of stylet 20, thereby to form a continuous or substantially continuous distal surface which is generally cone-shaped. The cone-shaped distal surface enables the combination of the outer tube member 12 and the stylet 20 to enter into the bone being biopsied with maximum smoothness and with the distal end being closed. If the surfaces of the distal end 18 and chiseled bevelled end 24 did not substantially line up, the continuity between them would increase the difficulty of the biopsy needle entering the bone.

In operation, the outer tube member 12 and the stylet 20 are engaged as shown in FIG. 2 in order to be inserted into the bone. After the outer tube 12 and the stylet 20 have been inserted into the bone marrow, the stylet 20 is withdrawn from the outer tube member 12, leaving the outer tube in the bone marrow. Next, an inner tube member 30 (FIG. 4) is inserted into the outer tube member 12 in order to take the bone marrow biopsy.

As shown in FIG. 4, the inner tube member 30 has a control knob 31 at its proximal end and a pair of pincers 32 at its distal end. The pincers 32 may be sharpened at their tips so as to more readily cut a biopsy core. The control knob 31 permits rotation of the inner tube member 30 within the outer tube member 12. The inner tube member 30 and outer tube member 12 contain a hole 33 through which a pin 35 can be inserted to lock the inner tube member 30 with respect to outer tube member 12.

As shown in FIGS. 7A and 7B, the distal end 18 of outer tube member 12 is generally oval in its cross-section and thereby has an elongated dimension and a narrow dimension. When the pincers 32 are aligned with the elongated dimension of the distal end 18 of the outer tube member 12 (FIGS. 6 and 7A), they are in an open position so as to receive the biopsy material in the general area of the distal end 18 of outer tube member 12. Upon rotation of the inner tube member 30 by rotation of control knob 31, the pincers 32 are aligned with the narrow dimension of distal end 18 and are caused to close upon themselves and thereby pinch off and grasp a sample of the bone marrow which is forward of the distal end 18 of outer tube member 12. The pincers 32 may have sharpened edges and/or their edges may be bent radially inwardly, so as to enhance the cutting action. The pincers 32 may be two opposed blades which are tapered at their distal ends, i.e., tweezer-like in structure. After the biopsy core has been pinched off and grasped by pincers 32, the outer and inner tube members 12 and 30 are withdrawn together from the bone, with the oval shaped distal end 18 continuing to hold the pincers 32 together in order to hold the sample during the process of withdrawal.

In a further embodiment of the biopsy needle, the distal end 18 of outer tube member 12 may be shaped to include oppositely disposed projections 34, as shown in FIGS. 8, 9A and 9B. In FIGS. 8 and 9A, pincers 32 are in an open position and are not engaged with the projections 34 so that they can thereby receive a sample of the bone marrow forward of the distal end 18. However, when the inner tube member 30 is rotated approximately 90° by turning control knob 31, the pincers 32 close upon themselves, as shown in FIG. 9B, and thereby pinch off and grasp a sample of the bone marrow. While a rotation of the inner tube member 30 by 90° may be sufficient to pinch off and grasp a biopsy needle, it may be necessary to continue further rotation of the control knob 31 to assure that a biopsy core has been completely severed from the bone marrow.

Although preferred embodiments have been described herein, many other variations and modifications and other uses will become apparent to those skilled in the art within the fair spirit and scope of the invention. The present invention, therefore, is not limited by the specific disclosure herein.

What is claimed is:

1. A biopsy needle for removing a biopsy core from a patient, said biopsy needle comprising:
    an outer tube member having a lumen therein, a proximal end and a distal end with an opening at the distal end for receiving a biopsy core, and oppositely disposed projections extending radially inward from said lumen and proximate the distal end;
    an inner tube member adapted to be slidable in said lumen of said outer tube member and having pincers at a distal end thereof, said inner tube member rotatable in said lumen, and by rotation thereof said pincers contact said oppositely disposed projections and thereby close upon each other to grasp a biopsy core.

2. The biopsy needle of claim 1, wherein said inner tube member is adapted to be rotatable so that said pincers are not in contact with said oppositely disposed projections and said pincers thereby are allowed to spread apart.

3. The biopsy needle of claim 1, further comprising:
    a locking mechanism which prevents said inner tube member from slidable and rotatable movement relative to said outer tube member.

4. The biopsy needle of claim 3, wherein said locking mechanism includes a pin and lateral openings in said inner tube member and said outer tube member, so that when said openings are aligned and said pin inserted therein, said inner and outer tube members are locked with respect to each other.

5. The biopsy needle of claim 1, wherein said pincers have edges bent radially inwardly, and thereby are capable of enhancing the cutting of a biopsy core of a patient.

6. The biopsy needle of claim 1, wherein said inner tube member and said pincers are unitary in structure.

7. The biopsy needle of claim 1, wherein said pincers include two opposed blades tapered at their distal ends.

8. The biopsy needle of claim 1, wherein said pincers are tweezer-like in structure.

9. The biopsy needle of claim 1, wherein said pincers have sharp edges, and thereby are capable of enhancing the cutting of a biopsy core from a patient.

10. A biopsy needle for removing a biopsy core from a patient, said biopsy needle comprising:
    an outer tube member having a lumen therein, a proximal end and a distal end with an opening at said distal end, proximate said distal end said outer tube member being generally oval in cross-section and thereby having an elongated dimension and a narrow dimension; and
    an inner tube member adapted to be slidable in and rotatable in said lumen of said outer tube member, said inner tube member having pincers at a distal end thereof, said pincers capable of being slidable in said outer tube member toward said distal end so that when said pincers are positioned proximate said distal end and in said elongated dimension said pincers are in an open position relative to each other, and when said pincers are positioned proximate said distal end and in said narrow dimension said pincers are in a closed position relative to each other to grasp a biopsy core.

11. The biopsy needle of claim 10, wherein said pincers are rotatable between said open and closed positions.

12. The biopsy needle of claim 10, further comprising:
    a locking mechanism which prevents said inner tube member from slidable and rotatable movement relative to said outer tube member.

13. The biopsy needle of claim 12, wherein said locking mechanism includes a pin and lateral openings in said inner tube member and said outer tube member, so that when said openings are aligned and said pin inserted therein said inner and outer tube members are locked with respect to each other.

14. The biopsy needle of claim 10, wherein said pincers have edges bent radially inwardly, and thereby capable of enhancing the cutting of a biopsy core of a patient.

15. The biopsy needle of claim 10, wherein said inner tube member and said pincers are unitary in structure.

16. The biopsy needle of claim 10, wherein said pincers include two opposed blades being tapered at their distal ends.

17. The biopsy needle of claim 10, wherein said pincers are tweezer-like in structure.

18. The biopsy needle of claim 10, wherein said pincers have sharp edges, and thereby are capable of enhancing the cutting of a biopsy core from a patient.

19. A biopsy needle for removing a biopsy core from a patient, said biopsy needle comprising:

an outer tube member having a lumen therein, a proximal end and a distal end with an opening at said distal end;

an inner tube member adapted to be slidable in and rotatable in said lumen of said outer tube member, said inner tube member having pincers at a distal end thereof; and means proximate the distal end of said outer tube member to cause said pincers of said inner tube member slid toward the distal end of said outer tube member to be open at a first position and upon rotation of said inner tube member to a second position relative to the outer tube member to cause said pincers to close toward each other thereby to grasp a biopsy core.

20. The biopsy needle of claim 19, further comprising:

a locking mechanism which prevents said inner tube member from slidable and rotatable movement relative to said outer tube member.

21. The biopsy needle of claim 20, wherein said locking mechanism includes a pin and lateral openings in said inner tube member and said outer tube member, so that when said openings are aligned and said pin inserted therein said inner and outer tube members are locked with respect to each other.

22. The biopsy needle of claim 19, wherein said pincers include two opposed blades tapered at their distal ends.

23. The biopsy needle of claim 19, wherein said pincers are tweezer-like in structure.

24. The biopsy needle of claim 19, wherein said pincers have sharp edges, and thereby are capable of enhancing the cutting of a biopsy core from a patient.

25. The biopsy needle of claim 19, wherein said pincers have edges are bent radially inwardly, and thereby are capable of enhancing the cutting of a biopsy core of a patient.

26. The biopsy needle of claim 19, wherein said inner tube member and said pincers are unitary in structure.

27. A method of removing a biopsy core of a patient using said biopsy needle of claim 10, comprising the steps of:

inserting said outer tube member in the area of the patient from which the biopsy core is to be taken;

sliding said inner tube member into said outer tube member and positioning said pincers about the biopsy core;

rotating the inner tube member relative to the outer tube member to cause said pincers to close about said biopsy core; and cutting off said biopsy core.

28. A method of removing a biopsy core of a patient using said biopsy needle of claim 1, comprising the steps of:

inserting said outer tube member in the area of the patient from which the biopsy core is to be taken;

sliding said inner tube member into said outer tube member and positioning said pincers about the biopsy core;

rotating the inner tube member relative to the outer tube member to cause said pincers to close about said biopsy core; and cutting off said biopsy core.

* * * * *